United States Patent [19]

De Beuckeleer et al.

[11] Patent Number: 5,589,610
[45] Date of Patent: Dec. 31, 1996

[54] STAMEN-SPECIFIC PROMOTERS FROM CORN

[75] Inventors: Marc De Beuckeleer; Lydia Herdies; Véronique Gossele, all of Gent, Belgium; Celestina Mariani, Nijmegen, Netherlands

[73] Assignee: Plant Genetic Systems, N.V., Belgium

[21] Appl. No.: 104,073

[22] PCT Filed: Feb. 5, 1992

[86] PCT No.: PCT/EP92/00275

§ 371 Date: Oct. 4, 1993

§ 102(e) Date: Oct. 4, 1993

[87] PCT Pub. No.: WO92/13957

PCT Pub. Date: Aug. 20, 1992

[30] Foreign Application Priority Data

Feb. 7, 1991 [EP] European Pat. Off. .............. 91400300
Jun. 28, 1991 [EP] European Pat. Off. .............. 91401787

[51] Int. Cl.⁶ ............... A01H 1/00; A01H 5/00; A01H 5/10; C12N 15/10; C12N 15/29

[52] U.S. Cl. ............ 800/205; 800/250; 800/DIG. 56; 435/172.3; 435/320.1; 435/240.4; 536/22.1; 536/23.6; 536/24.1; 536/24.5; 536/24.3; 935/6; 935/30; 935/35

[58] Field of Search ..................... 800/200, 205, 800/250, DIG. 52, DIG. 56; 435/240.1, 240.4, 240.48, 240.49, 240.5, 172.1, 172.3, 320.1; 536/23.6, 22.1, 24.5, 24.1, 24.3; 935/5, 9, 30, 35, 6

[56] References Cited

U.S. PATENT DOCUMENTS 5,086,169 2/1992 Mascarenhas .................. 536/27

FOREIGN PATENT DOCUMENTS 0344029 11/1989 European Pat. Off. .
WO90/08828 8/1990 WIPO .
WO90/08830 8/1990 WIPO .
WO91/02069 2/1991 WIPO .

OTHER PUBLICATIONS

Koltunow et al., "Different Temporal and Spatial Gene Expression Patterns Occur During Anther Development", *Plant Cell*, 2, 1201–1224 (1990).
Mariani et al., "Genetic Destruction of Tapetal Cells Results in the Production of Male Sterile Plants", *J. Cell. Biochem.*, Supplement15A, 21 (1991).
Rieger et al. 1976. Glossary of Genetics and Cytogenetics. Springer–Verlag. pp. 446+516.
Gordon–Kamm et al. 1990, The Plant Cell. 2:603–618.
Quattrocchio et al. 1990, Plant Molecular Biology. 15:81–83.

*Primary Examiner*—Erich E. Veitenheimer
*Attorney, Agent, or Firm*—Merchant, Gould, Smith, Edell, Welter & Schmidt, P.A.

[57] ABSTRACT

The invention relates to stamen-specific promoters derived from corn genes. These promoters includes two DNA sequences selected from sequences in SEQ ID NO:2 or SEQ ID NO:3. The invention also includes DNA including the stamen-specific promoters operably linked to a heterologous structural gene. The structural genes include those such as ribonuclease, barnase, and an A fragment of diphtheria toxin. The stamen-specific promoter may have its untranslated leader sequence replaced by the untranslated leader sequence of another gene. The invention also includes plant cells, plants, or seeds including these promoters and promoter-structural gene systems. The promoter may be in DNA that is stably integrated into the plant or seed.

37 Claims, No Drawings

5,589,610

1

STAMEN-SPECIFIC PROMOTERS FROM CORN

FIELD OF THE INVENTION

This invention relates to promoters isolated from corn which can provide gene expression predominantly or specifically in stamen cells of a plant, particularly a monocotyledonous plant, and thereby provide little or no gene expression in other parts of the plant that are not involved in the production of fertile pollen. The promoters are useful in the production of transformed plants, in which a gene is to be expressed at least predominantly, and preferably specifically, in the stamen cells, preferably in the anther cells. The promoters are especially useful in the production of male-sterile plants and male fertility-restorer plants as described in European patent applications ("EPA") 89401194.9 and 90402281.1, respectively (which are incorporated herein by reference), particularly in the production of hybrids of monocotyledonous plants, such as corn, rice or wheat.

SUMMARY OF THE INVENTION

In accordance with this invention are provided: male flower-specific cDNA sequences isolated from corn comprising the sequences, SEQ ID no. 1 and SEQ ID no. 2, shown in the sequence listing. Also in accordance with this invention are provided stamen-specific, preferably anther-specific, promoters of the corn genes corresponding to such cDNA sequences, particularly the promoter which controls the expression of the genomic coding sequence corresponding to the cDNA of SEQ ID no. 2 and which is contained within the sequence of nucleotides 1 to 1179 of SEQ ID no. 3 (the "CA55 promoter" or "PCA55"). Each of such promoters can be used in a foreign DNA sequence, preferably a foreign chimaeric DNA sequence, which contains a structural gene, preferably a male-sterility DNA or a male fertility-restorer DNA, under the transcriptional control of the promoter and which can be used to transform the nuclear genome of a cell of a plant, particularly a monocotyledonous plant. Further in accordance with this invention are provided: the male-sterile plant or male fertility-restorer plant which can be regenerated from such a cell transformed with the foreign DNA sequence of this invention; the transformed cell, itself; a culture of such a transformed cell; seeds of such a regenerated plant and its progeny; and a fertility-restored plant and its seeds resulting from crossing such male-sterile and male fertility-restorer plants.

DETAILED DESCRIPTION OF THE INVENTION

In accordance with this invention, a male-sterile plant or a male fertility-restorer plant can be produced from a single cell of a plant by transforming the plant cell in a known manner to stably insert, into its nuclear genome, the foreign DNA sequence of this invention. The foreign DNA sequence comprises at least one male-sterility DNA or male fertility-restorer DNA that is: under the control of, and fused in frame at its upstream (i.e., 5') end to, one of the stamen-specific, preferably anther-specific, particularly tapetum-specific, promoters of this invention, such as the promoter and optionally the leader sequence of SEQ ID no. 3; and fused at its downstream (i.e., 3') end to suitable transcription termination (or regulation) signals, including a polyadenylation signal. Thereby, the RNA and/or protein or polypeptide, encoded by the male-sterility or male fertility-restorer DNA, is produced or overproduced at least predominantly,

2 preferably exclusively, in stamen cells of the plant. The foreign DNA sequence can also comprise at least one marker DNA that: encodes a RNA and/or protein or polypeptide which, when present at least in a specific tissue or specific cells of the plant, renders the plant easily separable or distinguishable from other plants which do not contain such RNA and/or protein or polypeptide at least in the specific tissue or specific cells; is under the control of, and is fused at its 5' end to, a second promoter which is capable of directing expression of the marker DNA at least in the specific tissue or specific cells; and is fused at its 3' end to suitable transcription termination signals, including a polyadenylation signal. The marker DNA is preferably in the same genetic locus as the male-sterility or male fertility-restorer DNA. This linkage between the male-sterility or male fertility-restorer DNA and the marker DNA guarantees, with a high degree of certainty, the joint segregation of both the male-sterility or male fertility-restorer DNA and the marker DNA into offspring of the plant regenerated from the transformed plant cell. However in some cases, such joint segregation is not desirable, and in such cases, the marker DNA should be in a different genetic locus from the male-sterility or male fertility-restorer DNA.

The male-sterility DNA of this invention can be any gene or gene fragment, whose expression product (RNA and/or protein or polypeptide) disturbs significantly the metabolism, functioning and/or development of stamen cells, preferably anther cells, and thus prevents the production of fertile pollen. Preferred male-sterility DNAs are described in EPA 89401194.9, for example those DNAs encoding: RNases such as RNase T1 or barnase; DNases such as endonucleases (e.g., EcoRI); proteases such as papain; enzymes which catalyse the synthesis of phytohormones (e.g., isopentenyl transferase or the gene products of gene 1 and gene 2 of the T-DNA of Agrobacterium; glucanases; lipases; lipid peroxidases; plant cell wall inhibitors; or toxins (e.g., the A-fragment of diphtheria toxin or botulin). Other preferred examples of male-sterility DNAs are antisense DNAs encoding RNAs complementary to genes, the products of which are essential for the normal development of fertile pollen. Further preferred examples of male-sterility DNAs encode ribozymes capable of cleaving specifically given target sequences of genes encoding products which are essential for the production of fertile pollen. Still other examples of male-sterility DNAs encode products which can render stamen cells, particularly anther cells - and not other parts of the plant - susceptible to specific diseases (e.g. fungi or virus infection) or stress conditions (e.g. herbicides).

The construction of a vector comprising a male-sterility DNA, such as a barnase-encoding DNA, under the control of a corn anther-specific promoter of this invention, is most conveniently effected in a bacterial host organism such as *E. coli*. However, depending on the nature of the male-sterility DNA and the specific configuration of the vector, problems can be encountered due to the expression of the male-sterility DNA in, and the concurrent decrease of viability of, the host organism. Such problems can be solved in a number of ways. For instance, the host organism can be provided, on the same or a different plasmid from that containing the male-sterility DNA or even on its chromosomal DNA, with another DNA sequence that prevents or inhibits significantly the effect of the expression of the male-sterility DNA in the host organism. Such an other DNA sequence can encode, for example: an antisense RNA so that the accumulation and translation of the male-sterility RNA is prevented; or a protein. (e.g., barstar) which specifically inhibits the gene product of the male-sterility DNA (e.g., barnase; Hartley (1988) J. Mol. Biol. 202, 913). Alternatively, the male-sterility DNA can contain elements, such as a plant intron, which will only result in an active gene product in a plant cell environment. Examples of introns that can be used for this purpose are introns of the transcriptional units of: the adh-1 gene of maize (Luehrsen and Walbot (1991) Mol. Gen. Genet. 225, 81; Mascarenhas et al (1990) Plant Mol. Biol. 15, 913), the shrunken-1 gene of maize (Vasil et al (1989) Plant Physiol. 91, 1575), the cat-1 gene of castor bean (Tanaka et al (1990) Nucleic Acids Research ("NAR") 18, 6767), the act-1 gene of rice (McElroy et al (1990) The Plant Cell 2, 163; PCT publication WO 91/09948) and the TA36 gene (intron shown in SEQ ID no. 4).

The male fertility-restorer DNA of this invention can be any gene or gene fragment, whose expression product (RNA and/or protein or polypeptide) inactivates, neutralizes, inhibits, blocks, offsets, overcomes or otherwise prevents the specific activity of the product of a male-sterility DNA in stamen cells, particularly in anther cells. Preferred male fertility-restorer DNAs are described in EPA 90402281.1, for example those DNAs encoding: barstar which is the inhibitor of barnase; EcoRI methylase which prevents the activity of EcoRI; or protease inhibitors (e.g. the inhibitors of papain). Other examples of male fertility-restorer DNAs are antisense DNAs encoding RNAs complementary to male-sterility DNAs. Further examples of male fertility-restorer DNAs encode ribozymes capable of cleaving specifically given target sequences of male-sterility DNAs.

The marker DNA of this invention can be any gene or gene fragment encoding an RNA and/or protein or polypeptide that allows plants, expressing the marker DNA, to be easily distinguished and separated from plants not expressing the marker DNA. Examples of the marker DNA are described in EPA 89401194.9, such as marker DNAs which encode proteins or polypeptides that: provide a distinguishable color to plant cells, such as the A1 gene encoding dihydroquercetin-4-reductase (Meyer et al (1987) Nature 330, 677–678) and the glucuronidase gene (Jefferson et al (1988) Proc. Natl. Acad. Sci. USA ("PNAS") 83, 8447); provide a specific morphological characteristic to a plant such as dwarf growth or a different shape of the leaves; confer on a plant stress tolerance, such as is provided by the gene encoding superoxide dismutase as described in EPA 88402222.9; confer disease or pest resistance on a plant, such as is provided by a gene encoding a *Bacillus thuringiensis* endotoxin conferring insect resistance on a plant, as described in EPA 86300291.1; or confer on a plant a bacterial resistance, such as is provided by the bacterial peptide described in EPA 88401673.4. Preferred marker DNAs encode proteins or polypeptides inhibiting or neutralizing the activity of herbicides such as: the sfr gene and the sfrv gene encoding enzymes conferring resistance to glutamine synthetase inhibitors such as Bialaphos and phosphinotricine as described in EPA 87400544.0.

In order for the protein or polypeptide encoded by the marker DNA to function as intended, it is often preferred to have it produced in the plant cell as a precursor, in which the mature protein is linked at its N-terminal end to another polypeptide (a "targeting peptide") which will translocate the mature protein to a specific compartment such as the chloroplasts, the mitochondria, or the endoplasmic reticulum. Such targeting peptides and DNA sequences coding for them (the "targeting sequences") are well known. For example, if a marker DNA codes for a protein that confers tolerance or resistance to a herbicide or another selective agent that acts on chloroplast metabolism, such as the sfr (or bar) gene or the sfrv gene (European patent publication ("EP") 0,242,236), it may be preferred that such gene also comprise a chloroplast targeting sequence such as that coding for the transit peptide of the small subunit of the enzyme 1,5-ribulose bisphosphate carboxylase (Krebbers et al (1988) Plant Mol. Biol. 11, 745; EPA 85402596.2), although other targeting sequences coding for other transit peptides, such as those listed by Yon Heijne et al (1991) Plant Mol. Biol. Reporter 9, 104, can be used.

Each of the stamen-specific, preferably anther-specific, promoters of this invention, such as the CA55 promoter upstream from nucleotide 1180 in SEQ ID no. 3, which can be used to control the male-sterility DNA or the male fertility-restorer DNA, can be identified and isolated in a well known manner as described in EPA 89401194.9. In this regard, each of the SEQ ID no. 1 and no. 2 cDNAs of this invention can be used as a probe to identify (i.e., to hybridize to) the corresponding region of the corn genome (i.e., the region containing DNA coding for the stamen-specific mRNA, from which the cDNA was made). Then, the portion of the plant genome that is upstream (i.e., 5') from the DNA coding for such stamen-specific mRNA and that contains the promoter of this DNA can be identified. For instance, the cDNA of SEQ ID no. 2 can be used as a probe to identify and isolate a genomic clone from a genomic library of *Zea mays*, such as a lambda EMBL3 or EMBL4 *Zea mays* genomic library. In this way, a genomic DNA clone can be isolated and sequenced, such as the clone of SEQ ID no. 3. SEQ ID no. 3 contains a coding region which is homologous to the cDNA of SEQ ID no. 2, and upstream of this coding region is a promoter sequence, with a TATA box, which directs the anther-specific transcription of the coding region.

The second promoter, which controls the marker DNA, can also be selected and isolated in a well known manner, for example as described in EPA 89401194.9, so that the marker DNA is expressed either selectively in one or more specific tissues or cells or constitutively in the entire plant, as desired, depending on the nature of the RNA and/or protein or polypeptide encoded by the marker DNA.

In the foreign DNA sequence of this invention, 3' transcription termination signals or the "3' end" can be selected from among those which are capable of providing correct transcription termination and/or polyadenylation of mRNA in plant cells. The transcription termination signals can be the natural ones of the male-sterility or male fertility-restorer DNA, to be transcribed, or can be foreign or heterologous. Examples of heterologous 3' transcription termination signals are those of the octopine synthase gene (Gielen et al (1984) EMBO J. 3, 835–845) and of the T-DNA gene 7 (Velten and Schell (1985) NAR 13, 6981–6998). When the foreign DNA sequence of this invention comprises more than one structural gene (e.g., a male-sterility DNA or a fertility-restorer DNA and a marker DNA), it is preferred that the 3' ends of the structural genes be different.

In plants, especially in monocotyledonous plants, particularly cereals such as rice, corn and wheat, the expression in accordance with this invention of a marker DNA, as well as a male-sterility DNA or a fertility-restorer DNA, can be enhanced by the presence at one or more, preferably one, appropriate position(s) in the transcriptional unit of each foreign DNA sequence of this invention, of a suitable plant intron (Luehrsen and Walbot (1991) Mol. Gen. Genet. 225, 81; Mascarenhas et al (1990) Plant Mol. Biol. 15, 913; Vasil et al (1989) Plant Physiol. 91, 1575; Tanaka et al (1990) NAR 18, 6767; McElroy et al (1990) The Plant Cell 2, 163; PCT publication WO 91/09948). Preferably, each intron has a nucleotide sequence that: is recognizable by the cells of the plant species being transformed (for requirements of intron recognition by plants, see Goodall and Filipowicz (1989) Cell 58, 473; Hanley and Schuler (1988) NAR 16, 7159), is longer than about 70–73 bp (Goodall and Filipowicz (1990) Plant Mol. Biol. 14, 727), and is positioned close to the 5' end of the encoded mRNA, particularly in any untranslated leader sequence.

Cells of a plant can be transformed with the foreign DNA sequence of this invention in a conventional manner. Where the plant to be transformed is susceptible to Agrobacterium infection, it is preferred to use a vector, containing the foreign DNA sequence, which is a disarmed Ti-plasmid. The transformation can be carried out using procedures described, for example, in EP 0,116,718 and EP 0,270,822. Preferred Ti-plasmid vectors contain the foreign DNA sequence between the border sequences or at least located upstream of the right border sequence. Of course, other types of vectors can be used for transforming the plant cell, using procedures such as direct gene transfer (as described for example in EP 0,223,247), pollen mediated transformation (as described for example in EP 0,270,356, PCT publication W0/85/01856 and EP 0,275,069), in vitro protoplast transformation (as described for example in U.S. Pat. No. 4,684,611), plant virus-mediated transformation (as described for example in EP 0,067,553 and U.S. Pat. No. 4,407,956) and liposome-mediated transformation (as described for example in U.S. Pat. No. 4,536,475).

Where the plant to be transformed is corn, recently developed transformation methods can be used such as the methods described for certain lines of corn by Fromm et al (1990) Bio/Technology 8, 833 and Gordon-Kamm et al (1990) The Plant Cell 2, 603.

Where the plant to be transformed is rice, recently developed transformation methods can be used such as the methods described for certain lines of rice by Shimamoto et al (1990) Nature 338, 274, Datta et al (1990) Bio/Technology 8, 736, Christou et al (1991) Bio/Technology 9, 957 and Lee et al (1991) PNAS 88, 6389.

Where the plant to be transformed is wheat, a method analogous to those described above for corn or rice can be used. Preferably for the transformation of a monocotyledonous plant, particularly a cereal such as rice, corn or wheat, a method of direct DNA transfer, such as a method of biolistic transformation or electroporation, is used. When using such a direct transfer method, it is preferred to minimize the DNA that is transferred so that essentially only the foreign DNA sequence of this invention, with its male-sterility DNA, fertility-restorer DNA and/or marker DNA, is integrated into the plant genome. In this regard, when a foreign DNA sequence of this invention is constructed and multiplied on a plasmid in a bacterial host organism, it is preferred that, prior to transformation of a plant with the foreign DNA sequence, plasmid sequences that are required for propagation in the bacterial host organism, such as an origin of replication, an antibiotic resistance gene for selection of the host organism, etc., be separated from the parts of the plasmid that contain the foreign DNA sequence.

The Examples, which follow, describe: the isolation and the characterization of the two corn cDNA sequences SEQ ID no. 1 and no. 2 of this invention; their use for isolating the two stamen-specific promoters of this invention from the corn genome, such as the CA55 promoter upstream from nucleotide 1180 in SEQ ID no. 3; the construction of promoter cassettes for the fusion of the promoters with male-fertility and male fertility-restorer DNAs; the construction of plant transformation vectors from the promoter cassettes; as well as the transformation of corn, rice and tobacco with the resulting plant transformation vectors.

Unless stated otherwise in the Examples, all procedures for making and manipulating recombinant DNA were carried out by the standard procedures described in Maniatis et al, *Molecular Cloning*- A Laboratory Manual, cold Spring Harbor Laboratory Press, New York (1982) and Sambrook et al, *Molecular Cloning*- A Laboratory Manual, Second Edition, Cold Spring Harbor Laboratory Press, New York (1989). When making plasmid constructions, the orientation and integrity of cloned fragments were checked by means of restriction mapping and/or sequencing.

The sequence identification numbers referred to above and in the Examples are listed below.
Sequence Listing
SEQ ID no. 1: cDNA sequence of the CA444 gene.
SEQ ID no. 2: cDNA sequence of the CA455 gene.
SEQ ID no. 3: genomic DNA clone obtained from a *Zea mays* genomic library using the cDNA of SEQ ID no. 2 as a probe.
SEQ ID no. 4: intron from TA36 gene of *Nicotiana tabacum* linked to KpnI linkers
SEQ ID no. 5: sequence of plasmid pVE149.

EXAMPLE 1

Isolation and characterization of anther-specific cDNAs from corn

For the cloning of cDNAs corresponding to genes which are expressed exclusively, or at least predominantly, in anthers of corn, a cDNA library was prepared from poly A$^+$ mRNA isolated from tassel spikelets from the publicly available corn line B73 bearing anthers in tetrad stage. By means of the Amersham cDNA Synthesis System Plus RPN 1256 Y/Z kit (Amersham International PLC, Buckinghamshire, England), cDNA was synthesized using reverse transcriptase and an oligo dT primer according to the directions set forth in the kit for its use.

The cDNAs were cloned in lambda gt10 vector, using the Amersham cDNA Cloning System—lambda gt10—RPN1257—kit, in accordance with the directions set forth in the kit for its use. From the cDNA library thus obtained (30,000 plaques), differential screening was performed with a labelled cDNA probe from corn B73 seedlings and with a labeled cDNA probe from corn B73 whole spikelets. 93 possible anther-specific cDNA clones were selected and again screened with labeled cDNA probes from corn B73 anthers, seedlings and ears. With the 66 remaining clones from these additional selections, a Southern analysis was performed with differential cDNA probes from anthers at tetrad stage and from opened tassels, silk and ears from the corn line B73. This led to the selection of 27 anther-specific clones which were subcloned in pGEM1 (Promega, Madison, Wis., USA). Cross-hybridization between these subclones revealed the presence of at least 2 classes. Probes of some of these subclones were prepared and checked again for their specificity in Northern blots with 5 to 10 µg poly A$^+$ mRNA isolated from different corn B73 tissues (i.e., anthers, ears, silk, leaves, and spikelets at several stages). From this selection, two anther-specific clones, called "pCA444" and "pCA455", were identified. These clones were sequenced, and their sequences are shown in the sequence listing as SEQ ID no. 1 and SEQ ID no. 2, respectively. pCA455 was found to hybridize exclusively with mRNA from anthers in different stages of development. pCA444 was found to hybridize with mRNA from anthers and to hybridize very weakly with a mRNA of similar size from embryos.

The cDNA sequence of pCA444 reveals the presence of two open reading frames ("ORF") over a total of 323 and 376 nucleotides. The cDNA sequence of pCA455 reveals the presence of two ORFs over a total of 387 and 300 nucleotides.

EXAMPLE 2

Isolation of the anther-specific gene corresponding to the anther-specific cDNA clone, pCA444, of Example 1

To isolate the genomic DNA clones carrying the regulatory sequences of the gene, CA444, corresponding to pCA444, two approaches are taken.

The first approach uses inverse polymerase chain reactions ("PCR") (Ochman et al (1989) in "PCR: Application & Protocols", Innis, M., Gelfand, D., Sninsky, J., and White, T., eds. Academic Press, New York) for the geometric amplification of the DNA sequences which flank, upstream and downstream, a chosen core region of the CA444 gene sequence corresponding to the sequence of pCA444. DNA digestions are carried out using conventional buffers and well known conditions. Fragments of a suitable size (less than 3 to 4 kb) for correct amplification and circularization are produced by using restriction enzymes. which do not cleave the chosen core region of the CA444 gene sequence and which are preliminarily identified by Southern hybridization. Circularization is performed with T4 DNA ligase in a dilute DNA concentration favoring monomeric circles (Collins and Weissman (1984) PNAS 81, 6812–6815). Three polymerase chain reactions are performed in parallel with three different oligonucleotide pairs under conventional conditions (Saiki et al (1985) Science 230, 1250–1354) using the Vent™ DNA polymerase (Catalog no. 254L - Biolabs New England, Beverly, Mass. 01915, U.S.A.) isolated from *Thermococcus litoralis* (Neuner et al (1990) Arch. Micobiol. 153, 205–207).

In one reaction, the flanking regions of the core region of CA444, from nucleotide 85 to nucleotide 358 of the corresponding cDNA sequence (SEQ ID no. 1), are amplified using the following pair of 22 and 20 oligonucleotides having the following respective sequences:

1) 5' CCG AGG ACC AGC AGG ACG AGG C 3' (SEQ ID No: 6) (nucleotide 64 to nucleotide 85 of pCA444 (SEQ ID no. 1)) and 2) 5' GGA TGG CAG GAG GGG AGA GG 3' (SEQ ID NO: 7) (nucleotide 358 to nucleotide 377 of pCA444 (SEQ ID no. 1)).

In the second reaction, the flanking regions of the core region of CA444, from nucleotide 288 to nucleotide 392 of the corresponding cDNA sequence (SEQ ID no. 1), are amplified using the following pair of 20 and 23 oligonucleotides having the following respective sequences:

1) 5' GCA GGC TGT TGA TGA TGC CC 3' (SEQ ID NO: 20) (nucleotide 269 to nucleotide 288 of pCA444 (SEQ ID no. 1)) and 2) 5' CCA TTT CAC AGT GAG AGC AGT CG 3' (SEQ ID NO: 21) (nucleotide 392 to nucleotide 414 of pCA444 (SEQ ID no. 1)).

In the third reaction, the flanking regions of the core region of CA444, from nucleotide 43 to nucleotide 74 of the corresponding cDNA sequence (SEQ ID no. 1), are amplified using the following pair of 22 and 20 oligonucleotides having the following respective sequences:

1) 5' GGG GCG GTG GCT GCT TCT AGC G 3' (SEQ ID no: 8) (nucleotide 22 to nucleotide 43 of pCA444 (SEQ ID no. 1)) and 2) 5' GCT GGT CCT CGG CGG CGG CA 3' (SEQ ID no: 9) (nucleotide 74 to nucleotide 93 of pCA444 (SEQ ID no. 1)).

The second approach uses a lambda EMBL3 or EMBL4 *Zea mays* genomic library that is screened with the whole cDNA sequence of pCA444 as a probe. Corresponding genomic clones which hybridize to pCA444 are sequenced (Maxam and Gilbert (1977) PNAS 74, 560) and their orientation checked by Northern blot analysis with riboprobes of both senses. Comparison of the sequences of pCA444 with the genomic clone sequences leads to the identification of the homologous regions. At the 5' end of the region of each of these homologous genomic clones, the ATG codon and the consensus sequence TATA are determined. That the "TATA"-box is part of the promoter is confirmed by primer extension.

EXAMPLE 3

Isolation of the anther-specific gene corresponding to the anther-specific cDNA clone, pCA455, of Example 1

To isolate the genomic DNA clones carrying the regulatory sequences of the gene, CA455, corresponding to pCA455, the two approaches of Example 2 are used.

In the first approach, inverse PCR (Ochman et al, 1989) is used for the geometric amplification of the DNA sequences which flank a chosen core region of the CA455 gene sequence corresponding to the sequence of pCA455. DNA digestion and circularization are carried out as in Example 2. Two polymerase chain reactions are performed in parallel with two different oligonucleotide pairs under conventional conditions (Saiki et al, 1985) using the Vent™ DNA polymerase isolated from *T. litoralis* (Neuner et al, 1990).

In one reaction, the flanking regions of the core region of CA455, from nucleotide 54 to nucleotide 87 of the corresponding cDNA sequence (SEQ ID no. 2), are amplified using the following pair of 21 and 23 oligonucleotides having the following respective sequences:

1) 5' GCT CGA TGT ATG CAG TGC AGC 3' (SEQ ID NO. 10) (nucleotide 34 to nucleotide 54 of pCA455 (SEQ ID no. 2)) and 2) 5' CGT CGC CGT GTC GGT GCT TCT CG 3' (SEQ ID NO. 11) (nucleotide 87 to nucleotide 109 of pCA455 (SEQ ID no. 2)).

In the second reaction, the flanking regions of the core region of CA455, from nucleotide 54 to nucleotide 557 of the corresponding cDNA sequence (SEQ ID no. 2), are amplified using the following pair of 21 and 24 oligonucleotides having the following respective sequences:

1) 5' GCT CGA TGT ATG CAG TGC AGC 3' (SEQ ID No. 10) (nucleotide 34 to nucleotide 54 of pCA455 (SEQ ID no. 2)) and 2) 5' CCG TTG CGT TGC GTT GCG TAG ACG 3' (SEQ ID No. 12) (nucleotide 557 to nucleotide 580 of pCA455 (SEQ ID no. 2)).

The second approach uses a lambda EMBL3 or EMBL4 *Zea mays* genomic library that is screened with the whole cDNA sequence of pCA455 as a probe. Corresponding genomic clones which hybridize to pCA455 are sequenced (Maxam and Gilbert, 1977), and their orientation is checked by Northern blot analysis with riboprobes of both senses. Comparison of pCA455 with the genomic clone sequences leads to the identification of the homologous regions. At the 5' end of the region of each of these homologous genomic clones, the ATG codon and the consensus sequence TATA are determined. That the "TATA"-box is part of the promoter is confirmed by primer extension.

Using this second approach, an existing lambda EMBL4 *Zea mays* genomic library was screened with the whole cDNA sequence of pCA455, as a probe. The library was obtained from Dr. H. Saedler of the Max Planck Institute in Köln, Germany, with the designation "GH#1417". The library comprised *Zea mays* genomic DNA which was partially digested with MboI and the resulting restriction fragments of which were cloned between the BamHI sites of the bacteriophage lambda EMBL4 replacement vectors (Frischauff et al (1983) J. Mol. Biol. 170, 827; Pouwels et al (1988) *Cloning vectors*—a Laboratory Manual (supplementary update), Elsevier Science Publishers, Amsterdam). The restriction fragments of the library could be excised from the vectors as EcoRI fragments.

One EcoRI fragment of about 6 kb in length from the library was found to hybridize with pCA455 and was called "VG55". VG55 was found to contain an unique BamHI site, and one of the EcoRI-BamHI fragments of VG55 still hybridized with pCA455 while the other did not. The EcoRI-BamHI fragment that cross-hybridized with pCA455 was cloned between the EcoRI and BamHI sites of vector pGEM1 (Promega), yielding a plasmid called "pVG55.3". pVG55.3 was sequenced (Maxam and Gilbert, 1977), and its orientation was checked by Northern blot analysis with riboprobes of both senses. The sequence of pVG55.3, apart from some nucleotides at its 5' end (which includes its EcoRI site), is shown in SEQ ID no. 3 as having a high degree of homology with pCA455. The ATG codon of the presumed coding sequence of pVG55.3 is located at position 1180, the presumed coding sequence ends at position 1596, and the "TATA"-box is located at position 1072. That the "TATA"-box is part of the promoter is confirmed by primer extension. The unique BamHI site, mentioned above, is located at position 2770 in SEQ ID no. 3.

The sequence upstream from position 1180 in SEQ ID no. 3 can be used as a promoter region for the anther-specific expression of a coding sequence of interest. This sequence is the CA55 promoter or PCA55. Preferably, the complete sequence from position 1 to position 1179 is used, but it appears that the minimum region which can serve as an anther-specific promoter extends about 300 to 500 bp upstream from position 1180 in SEQ ID no. 3. The use of the untranslated leader sequence in the PCA55 promoter region, between the transcription initiation site (which can be determined by means of primer extension) and the ATG start of translation, appears to be preferred but not essential for anther-specific expression of a heterologous structural gene under the control of the PCA55 promoter, and the leader sequence apparently can be replaced by the untranslated leader sequence of other genes, such as plant genes.

EXAMPLE 4

Construction of promoter cassettes derived from the anther-specific genes of Examples 2 and 3

The 5' regulatory sequences, including the promoter, of each of the anther-specific genes of Examples 2 and 3 are subcloned into the polylinker of pMa5-8 and pMc5-8 (EPA 87402348.4). This produces vectors which can be used to isolate single stranded DNA for use in site-directed mutagenesis. Using site-directed mutagenesis (EPA 87402348.4), sequences surrounding the ATG translation initiation codon of the 5' regulatory sequences of each of the anther-specific genes are modified to create a unique recognition site for a restriction enzyme for which there is a corresponding recognition site at the 5' end of each of the male-sterility and male fertility-restorer DNAs (that are to be fused to the 5' regulatory sequences in Example 5, below). The resulting plasmids each contain the newly created restriction site. The precise nucleotide sequence spanning each newly created restriction site is determined in order to confirm that it only differs from the 5' regulatory sequences of the corresponding corn anther-specific gene by the substitution, creating the new restriction site.

In using this procedure for constructing promoter cassettes, a NcoI site is introduced at the ATG translation initiation codon of pVG55.3 of Example 3 as follows. A 1280 bp EcoRI-AvaI fragment of pVG55.3 (the AvaI site is located at position 1276 of SEQ ID no. 3; the EcoRI site is derived from pGEM1 (Promega) and is located at the 5' end of SEQ ID no. 3 [not shown]) is cloned between the EcoRI and AvaI sites of the vectors pMa5-8 and pMc5-8 (Stanssens et al (1989) NAR 17, 4441; EPA 87402348.4), yielding plasmids called "pMa5-VG55.3" and "pMc5-VG55.3", respectively These plasmids are used for site-directed mutagenesis by a gapped duplex DNA method using alternating selectable markers as described by Stanssens et al (1989) supra. The gapped duplex DNA is constructed from the single stranded pMc5-VG55.3 and the large EcoRI-AvaI fragment of pMa5-VG55.3. For mutagenesis, use is made of the oligonucleotide with the following sequence:

CAG GAG CGA GCC ATG GCT GCA G (SEQ ID no: 13).

This mutagenesis introduces the NcoI site at the ATG codon of the coding sequence of SEQ ID no. 3. The resulting cassette comprises the promoter and leader sequence of SEQ ID no. 3 in a EcoRI-NcoI fragment that is to be fused to the coding sequences of male-sterility and male fertility-restorer DNAs as described in Example 5, below.

Alternatively, the NcoI site is introduced at the ATG translation initiation codon of pVG55.3 during amplification by PCR of a DNA fragment, containing the CA55 promoter region, using the following two oligonucleotides as primers:

5'-GAT TCG AAT TCT GGT ATG CAT CAA TAG AGC CG-3' (SEQ ID no: 14)

5'-CAG GAG CGA GCC ATG GCT GCA G-3' (SEQ ID no: 13)

The amplified DNA fragment is used directly as a promoter cassette for constructing plant transformation vectors as described in Example 5.

EXAMPLE 5

Construction of plant transformation vectors from the promoter cassettes of Example 4

Using the procedures described in EPA 89401194.9 and 90402281.1, the promoter cassettes of Example 4 are used to construct plant transformation vectors comprising foreign chimaeric DNA sequences of this invention, each of which contains the 5' regulatory sequences, including the anther-specific promoter, of one of the anther-specific genes isolated in Example 2 or 3. Each of these 5' regulatory sequences is upstream of, is in the same transcriptional unit as, and controls either a male-sterility DNA (from EPA 89401194.9) encoding barnase from *Bacillus amyloliguefaciens* (Hartley and Rogerson (1972) Preparative Biochemistry 2 (3), 243–250) or a male fertility-restorer DNA (from EPA 90402281.1) encoding barstar (Hartley and Rogerson (1972) supra; Hartley and Sweaton (1973) J. Biol. Chem. 248 (16), 5624–5626). Downstream of each male-sterility or male fertility-restorer DNA is the 3' end of the nopaline synthase gene (An et al (1985) EMBO J. 4 (2), 277). Each chimaeric DNA sequence also comprises the 35 S'3 promoter (Mull and Howell (1987) Virology 86, 482–493) fused in frame with the neo gene encoding kanamycin resistance (EPA 84900782.8) and the 3' end of the octopine synthase gene (Dhaese et al (1983) EMBO J. 2, 419).

Alternatively, the plant transformation vectors pVE149, pVE139 and pVE136 are constructed as follows.

In a first step, the 1083 bp EcoRI-HindIII DNA fragment of pMT416, containing the barnase and barstar coding sequences (Hartley (1988) J. Mol. Biol. 202, 913), is ligated to the large EcoRI-HindIII fragment of plasmid pMa5-8, yielding plasmid pMa5tpbsl. By means of site-directed mutagenesis (PCT publication WO 89/03887), a NcoI site is then introduced at the ATG translation initiation codon of the barnase coding sequence. For this purpose, a gapped duplex DNA is constructed from the single stranded pMa5tpbsl, the large EcoRI-HindIII fragment of pMc5-8, and the following oligonucleotide:

5'-GAT AAC CGG TAC CAT GGT TGT CAC AGG GG-3' (SEQ ID no: 15).

The resulting plasmid is designated as "pVE145A".

In a subsequent mutagenesis round, a NsiI site is introduced 14 bp downstream of the ATG translation initiation codon of the barnase coding sequence using a gapped duplex DNA consisting of single stranded DNA from pVE145A, the large EcoRI-HindIII fragment of pMa5-8, and the following oligonucleotide:

5'-CCC CGT CAA ATG CAT TGA TAA CCG G-3' (SEQ ID no: 16).

The resulting plasmid is designated as "pVE145".

Plasmids pMa5-8 and pMc5-8 have been deposited on May 3, 1988 at the Deutsche Sammlung fur Mikroorganismen und Zellkulturen (DSM), Mascheroderweg 1B, D-330 Braunschweig, Germany under accession numbers DSM 4567 and DSM 4566 respectively.

pVE145 is cut with NsiI, filled in with Klenow, and ligated to the 111 bp DNA fragment shown in SEQ ID no. 4 which contains the TA36 intron and which has been cleaved with KpnI and made blunt-ended with Klenow, yielding plasmid pVE146. The fragment of SEQ ID no. 4 is obtained by amplification, from genomic DNA of Nicotiana tabacum cv. Samsun, by means of PCR using the following two oligonucleotides as primers:

5'-CGA CGG TAC CAC GTA ATT AG-3' (SEQ ID no: 17)

5'-CAT AGG GTA CCT GTA TGT AAT AAA AAC-3' (SEQ ID no: 18).

Plasmid pVE147 is constructed by ligation of the 2820 bp EcoRI-HindIII fragment of pGEM1 (Promega), the 979 bp HindIII-NcoI fragment of pVE146 (carrying the barnase gene with intron), and the 1184 bp PCR fragment of Example 4 carrying the CA55 anther-specific promoter from corn.

Finally, pVE149 is obtained by ligation of the following four DNA fragments:

the 1715 bp EcoRI (filled-in with Klenow)—XbaI fragment of pVE147, carrying the barnase gene under control of the CA55 promoter, a 296 bp EcoRI-XbaI fragment of pTTM6 (deposited on Mar. 7, 1988 at the DSM under DSM accession number 4468), carrying the 3' untranslated end of the nopaline synthase gene of Agrobacterium T-DNA, a 1728 bp BglII (filled-in with Klenow)-HindIII fragment, carrying the bar gene (EP 0,242,236) under the control of the 35S3 promoter (EP 0,359,617) and with a 3' untranslated end of the nopaline synthase gene of Agrobacterium T-DNA (this fragment corresponds to the sequence in SEQ ID no. 5 between positions 2409 and 4137), and the large EcoRI-HindIII fragment of pUC19 (New England Biolabs Inc. Beverly, Mass., U.S.A.).

The complete sequence of pVE149 is shown in SEQ ID no. 5.

Plasmid pVE136 is identical to pVE149 except it lacks the TA36 intron in the barnase gene. pVE136 is constructed by replacing, in pVE149, the 534 bp NcoI-BamHI fragment, carrying the barnase gene, with the 449 bp NcoI-BamHI fragment of pVE145A.

pVE136 is constructed and maintained in E. coli WK6 containing the plasmid pMc5-BS. pMc5-BS contains the barstar gene under the control of the tac promoter (De Boer et al (1983) PNAS 80, 21) and is constructed by cloning the EcoRI-HindIII fragment of pMT416 (Hartley (1988) J.Mol.Biol. 202, 913) into pMc5-8. Then, the sequence, starting with the PhoA signal sequence and ending with the last nucleotide before the translation initiation codon of the barstar coding region, is deleted by looping-out mutagenesis according to the general procedures described by Sollazi et al (1985) Gene 37, 199. The availability of an ampicillin resistance gene on the pUC18-derived plasmids carrying the chimaeric barnase gene and the chloramphenicol resistance gene on pMc5-BS permits the strain to be kept stable on plates provided with two antibiotics or to select for any one plasmid. While normally repressed, gene expression from this promoter can be induced by addition of a commonly used inducer of the lac operon, IPTG (isopropyl-$\beta$-d-thiogalactopyranoside).

The 5843 bp NcoI-BamHI fragment of partially digested pVE149, carrying all of the plasmid except the barnase coding sequence, is filled in with Klenow and ligated to a DraI-HindIII fragment (filled-in with Klenow) of pVE151, carrying the barstar coding sequence. The resulting plasmid is designated as "pVE139". pVE151 is obtained by means of site-directed mutagenesis of pMc5-BS, so that a DraI site is introduced at the ATG translation initiation codon of the barstar coding sequence. For this purpose, a gapped duplex DNA is constructed from the single stranded pMc5-BS, the large EcoRI-HindIII fragment of pMa5-8, and the following oligonucleotide:

5'-GCT TTT TTA AAT TTA TTT TCT CC-3' (SEQ ID no: 19).

T-DNA vectors for Agrobacterium-mediated plant transformations are prepared by cloning the appropriate EcoRI (filled-in with Klenow)-HindIII fragments of pVE149 or pVE136 (containing the 35S3-bar and corn anther-specific promoter-barnase chimaeric genes) or pVE139 (containing the 35S3-bar and corn anther-specific promoter-barstar chimaeric genes) between the HindIII and XbaI (filled-in with Klenow) sites of the known T-DNA vectors pGSC1700 or pGSC1701A. pGSC1700 has been deposited on Mar. 21, 1988 at the DSM under DSM accession number 4469, and pGSC1701A has been deposited on Oct. 22, 1987 at the DSM under DSM accession number 4286. The T-DNA vectors containing pVE149, pVE139 and pVE136 are used for transformation of tobacco as described in Example 7.

EXAMPLE 6

Transformation of corn with the plant transformation vectors from Example 5.

Using the procedures described by Fromm et al (1990) supra, embryogenic suspension cultures of a B73×A188 corn line are transformed with the plant transformation vectors described in Example 5, including pVE149, pVE136 and pVE139—either directly or after suitable linearization (e.g., after digestion with EcoRI and/or HindIII). Transformed plants regenerated from the embryogenic suspension cultures, each containing an anther-specific promoter of Example 2 or 3 controlling either a male-sterility DNA or a male fertility-restorer DNA, are normal except for their flowers. In this regard, each plant containing a male-sterility DNA under the control of one of the anther-specific promoters expresses such DNA at least predominantly in its anthers and produces no normal pollen, and each plant containing a male fertility-restorer DNA under the control of one of the anther-specific promoters expresses such DNA at least predominantly in its anthers but produces normal pollen.

EXAMPLE 7

Transformation of tobacco with the plant transformation vectors from Example 5

Using the procedures described in EPA 89401194.9 and 90402281.1, tobacco plants are transformed by Agrobacterium-mediated transfer with the plant transformation vectors containing the foreign chimaeric DNA sequences from Example 5. The transformed tobacco plants, each containing an anther-specific promoter of Example 2 or 3 controlling either a male-sterility DNA or a male fertility-restorer DNA, are normal except for their flowers. In this regard, each plant containing a male-sterility DNA under the control of one of the anther-specific promoters expresses such DNA at least predominantly in its anthers and produces no normal pollen, and each plant containing a male fertility-restorer DNA under the control of one of the anther-specific promoters expresses such DNA at least predominantly in its anthers but produces normal pollen.

EXAMPLE 8

Transformation of rice with the plant transformation vectors from Example 5

Using the procedures described by Datta et al (1990) supra, protoplasts of the rice line, Oryza sativa var. Chinsurah Boro II, are transformed with the plant transformation vectors described in Example 5, including pVE149, pVE136 and pVE139—either directly or after suitable linearization (e.g., after digestion with EcoRI and/or HindIII). Transformed plants regenerated from the protoplasts, each containing an anther-specific promoter of Example 2 or 3 controlling either a male-sterility DNA or a male fertility-restorer DNA, are normal except for their flowers. In this regard, each plant containing a male-sterility DNA under the control of the anther-specific promoters expresses such DNA at least predominantly in its anthers and produces no normal pollen, and each plant containing a male fertility-restorer DNA under the control of the anther-specific promoter expresses such DNA at least predominantly in its anthers but produces normal pollen. Alternatively, immature embryos from rice varieties Gulfmont, Lemont, IR26, IR36, IR54, or IR72 are bombarded with gold particles, carrying appropriate plasmid DNA of Examples 5, and plants are regenerated according to the procedures described by Christou et al (1991) Bio/Technology 9, 957.

Needless to say, the use of the anther-specific corn promoters of this invention is not limited to the transformation of any specific plant(s). Such corn promoters can be useful in any crop where they are capable of controlling gene expression, and preferably where such expression occurs at least predominantly, preferably specifically, in stamen cells of the crop. Also, the use of such promoters is not limited to the control of male-sterility DNAs or male fertility-restorer DNAs but can be used to control the expression of any gene selectively in stamen cells.

Furthermore, this invention is not limited to the specific stamen-specific, preferably anther-specific, particularly tapetum-specific, promoters described in the foregoing Examples. Rather, this invention encompasses promoters equivalent to those of Examples 2 and 3 which can be used to control the expression of a structural gene, such as a male-sterility DNA or a male fertility-restorer DNA, selectively in stamen cells, preferably anther cells, particularly tapetum cells, of a plant. Indeed it is believed that the DNA sequences of the promoters of Examples 2 and 3 can be modified by replacing some of their nucleotides with other nucleotides, provided that such modifications do not alter substantially the ability of polymerase complexes, including transcription activators, of stamen cells, particularly anther cells, to recognize the promoters, as modified.

We claim:

1. A stamen-specific promoter of a corn gene, said corn gene encoding a mRNA wherein a cDNA of said mRNA comprises a first DNA sequence and a second DNA sequence, wherein:
   (a) said first DNA sequence is complementary to a sequence of 21 to 24 nucleotides of the DNA of SEQ ID No. 2 or is complementary to a sequence of 21 to 24 nucleotides of the DNA of SEQ ID No. 3 between positions 1120 and 18391; and
   (b) said second DNA sequence corresponds to a sequence of 21 to 24 nucleotides of the DNA of SEQ ID No. 2 or corresponds to a sequence of 21 to 24 nucleotides of the DNA of SEQ ID No. 3 between positions 1120 and 1839, and wherein said second DNA sequence is located in said cDNA downstream of said first DNA sequence.

2. The stamen-specific promoter of claim 1 wherein said first DNA sequence is

5' GCT CGA TGT ATG CAG TGC AGC 3' which corresponds to SEQ ID No. 10.

3. The stamen-specific promoter of claim 1 wherein said second DNA sequence is selected from the group consisting of:

5' CGT CGC CGT GTC GGT GCT TCT CG 3' which corresponds to SEQ ID No. 11 and

5' CCG TTG CGT TGC GTT GCG TAG ACG 3' which corresponds to SEQ ID No. 12.

4. A foreign DNA comprising the promoter of claim 1 operably linked to a heterologous structural gene.

5. A foreign DNA comprising a DNA encoding a ribonuclease operably linked to the promoter of claim 1.

6. A foreign DNA comprising a DNA encoding a barnase operably linked to the promoter of claim 1.

7. A foreign DNA comprising a DNA encoding an A fragment of diphtheria toxin operably linked to the promoter of claim 1.

8. A foreign DNA comprising a DNA encoding a barstar operably linked to the promoter of claim 1.

9. A stamen-specific promoter region, wherein said promoter region is contained within the sequence of nucleotides 1 to 1179 of SEQ ID No. 3.

10. The stamen-specific promoter region of claim 9, wherein said promoter region comprises the sequence of SEQ ID No. 3 between nucleotide position 880 and nucleotide position 1179.

11. The stamen-specific promoter region of claim 9 wherein said promoter region comprises the sequence of SEQ ID No. 3 between nucleotide position 680 and nucleotide position 1179.

12. The stamen-specific promoter region of claim 9 wherein said promoter region has the sequence of SEQ ID No. 3 between nucleotide position 1 and nucleotide position 1179.

13. The stamen-specific promoter region of claim 9 in which the untranslated leader sequence is replaced by the untranslated leader sequence of another gene.

14. A foreign DNA comprising the promoter region of claim 9 operably linked to a heterologous structural gene.

15. A foreign DNA comprising a DNA encoding a ribonuclease operably linked to the promoter region of claim 9.

16. A foreign DNA comprising a DNA encoding a barnase operably linked to the promoter region of claim 9.

17. A foreign DNA comprising a DNA encoding an A fragment of a diphtheria toxin operably linked to the promoter region of claim 9.

18. A foreign DNA comprising a DNA encoding a barstar operably linked to the promoter region of claim 9.

19. A plant cell containing stably integrated in its genome a foreign DNA comprising the promoter region of claim 9 operably linked to a heterologous structural gene.

20. A plant cell containing stably integrated in its genome a foreign DNA comprising a DNA encoding a ribonuclease operably linked to the promoter region of claim 9.

21. A plant cell containing stably integrated in its genome a foreign DNA comprising a DNA encoding a barnase operably linked to the promoter region of claim 9.

22. A plant cell containing stably integrated in its genome a foreign DNA comprising a DNA encoding an A fragment of a diphtheria toxin operably linked to the promoter region of claim 9.

23. A plant cell containing stably integrated in its genome a foreign DNA comprising a DNA encoding a barstar operably linked to the promoter region of claim 9.

24. A plant or seed containing stably integrated in the genome of its cells a foreign DNA comprising the promoter region of claim 9 operably linked to a heterologous structural gene.

25. A plant or seed containing stably integrated in the genome of its cells a foreign DNA comprising a DNA encoding a ribonuclease operably linked to the promoter region of claim 9.

26. A plant or seed containing stably integrated in the genome of its cells a foreign DNA comprising a DNA encoding a barnase operably linked to the promoter region of claim 9.

27. A plant or seed containing stably integrated in the genome of its cells a foreign DNA comprising a DNA encoding an A fragment of diphtheria toxin operably linked to the promoter region of claim 9.

28. A plant or seed containing stably integrated in the genome of its cells a foreign DNA comprising a DNA encoding a barstar operably linked to the promoter region of claim 9.

29. A stamen-specific promoter region, wherein said promoter region has the sequence of SEQ ID No. 5 between nucleotide position 1224 and nucleotide position 2408.

30. The stamen-specific promoter region of claim 29 in which the untranslated leader sequence is replaced by the untranslated leader sequence of another gene.

31. A plant or seed containing stably integrated in the genome of its cells a foreign DNA comprising the promoter region of claim 29 operably linked to a heterologous structural gene.

32. A plant or seed containing stably integrated in the genome of its cells a foreign DNA comprising a DNA encoding a ribonuclease operably linked to the promoter region of claim 29.

33. A plant or seed containing stably integrated in the genome of its cells a foreign DNA comprising a DNA encoding a barnase operably linked to the promoter region of claim 29.

34. A plant or seed containing stably integrated in the genome of its cells a foreign DNA comprising a DNA encoding an A fragment of diphtheria toxin operably linked to the promoter region of claim 29.

35. A plant or seed containing stably integrated in the genome of its cells a foreign DNA comprising a DNA encoding a barstar operably linked to the promoter region of claim 29.

36. A pair of oligonucleotides for isolating a stamen-specific promoter from corn, said pair of oligonucleotides consisting of:

(a) a first oligonucleotide complementary to a sequence of 21 to 24 nucleotides of the DNA of SEQ ID No. 2 or complementary to a sequence of 21 to 24 nucleotides of the DNA of SEQ ID No. 3 between nucleotide positions 1120 and 1839; and (b) a second oligonucleotide corresponding to a sequence of 21 to 24 nucleotides of the DNA of SEQ ID No. 2 or corresponding to a sequence of 21 to 24 nucleotides of the DNA of SEQ ID No. 3 between nucleotide positions 1120 and 1839.

37. The oligonucleotides of claim 36, wherein said first oligonucleotide has the following sequence:

5' GCT CGA TGT ATG CAG TGC AGC 3' which corresponds to SEQ ID No. 10 and the second oligonucleotide has a sequence selected from the group consisting of:

5' CGT CGC CGT GTC GGT GCT TCT CG 3' which corresponds to SEQ ID No. 11 and

5' CCG TTG CGT TGC GTT GCG TAG ACG 3' which corresponds to SEQ ID No. 12.

\* \* \* \* \*

UNITED STATES PATENT AND TRADEMARK OFFICE
CERTIFICATE OF CORRECTION

PATENT NO. : 5,589,610

DATED : DECEMBER 31, 1996

INVENTOR(S) : DE BEUCKELEER ET AL.

It is certified that error appears in the above-identified patent and that said Letters Patent is hereby corrected as shown below:

Column 35, line 41, "18391" should read ---1839---.

Signed and Sealed this

Second Day of February, 1999

Attest:

Attesting Officer

*Acting Commissioner of Patents and Trademarks*

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
      ( A ) LENGTH: 533 base pairs
      ( B ) TYPE: nucleic acid
      ( C ) STRANDEDNESS: double
      ( D ) TOPOLOGY: linear ( i i ) MOLECULE TYPE: cDNA to mRNA ( v i ) ORIGINAL SOURCE:
      ( A ) ORGANISM: Corn
      ( F ) TISSUE TYPE: anther ( v i i ) IMMEDIATE SOURCE:
      ( A ) LIBRARY: cDNA designated as CA444

( i x ) FEATURE:
      ( A ) NAME/KEY: misc_feature (B) LOCATION: 2..376
(D) OTHER INFORMATION: /function= "Open Reading Frame 1"

(ix) FEATURE:
(A) NAME/KEY: misc_feature
(B) LOCATION: 3..326
(D) OTHER INFORMATION: /function= "Open Reading Frame 2"

(xi) SEQUENCE DESCRIPTION: SEQ ID NO:1:

| | | | | | | |
|---|---|---|---|---|---|---|
| GGATCCTCGA | GGCAACAATG | GCGCTAGAAG | CAGCCACCGC | CCCCCGCGCA | CTCCTCGCCG | 60 |
| CGTGCCTCGT | CCTGCTGGTC | CTCGGCGGCG | GCACCGGCCC | GTCGTCGGTG | CTGCGCGGCG | 120 |
| CCGGGGCGCA | GGCCGGCGGG | CAGTGCCTGC | CGCAGCTGAA | CCGCCTCCTG | GCGTGCCGCG | 180 |
| CGTACCTGGT | GCCCGGCGCG | CCGGACCCCA | GCGCGGACTG | CTGCAGCGCG | CTGAGCGCCG | 240 |
| TGTCGCACGA | GTGCGCCTGC | AGCACCATGG | GCATCATCAA | CAGCCTGCCC | GGCCGGTGCC | 300 |
| ACCTCGCCCA | AGCCAACTGC | TCCGCTTGAA | GCAGGGACCT | GGCACGCGTG | CTGCAATGGA | 360 |
| TGGCAGGAGG | GGAGAGGAAT | AAGAAGTGTT | TCCATTTCAC | AGTGAGAGCA | GTCGAGCTCC | 420 |
| AACGTTGTCG | TCGTCGTCGT | CTTCTTCTTT | TGATATTCAG | ACTCTGTCTT | GCGGTCTATA | 480 |
| TCATCAGCAT | AATAATAATA | AATAAGTAA | AACCAAAAAA | AAAAAAAAC | CAT | 533 |

(2) INFORMATION FOR SEQ ID NO:2:

(i) SEQUENCE CHARACTERISTICS:
(A) LENGTH: 796 base pairs
(B) TYPE: nucleic acid
(C) STRANDEDNESS: double
(D) TOPOLOGY: linear (ii) MOLECULE TYPE: cDNA to mRNA (vi) ORIGINAL SOURCE:
(A) ORGANISM: Corn
(F) TISSUE TYPE: anther (vii) IMMEDIATE SOURCE:
(A) LIBRARY: cDNA designated as CA455

(ix) FEATURE:
(A) NAME/KEY: misc_feature
(B) LOCATION: 2..388
(D) OTHER INFORMATION: /function= "Open Reading Frame 1"

(ix) FEATURE:
(A) NAME/KEY: misc_feature
(B) LOCATION: 70..369
(D) OTHER INFORMATION: /function= "Open Reading Frame 2"

(xi) SEQUENCE DESCRIPTION: SEQ ID NO:2:

| | | | | | | |
|---|---|---|---|---|---|---|
| CCATGGTACC | CGGATCCTCG | CCAAAACGCA | GAAGCTGCAC | TGCATACATC | GAGCTAACTA | 60 |
| TCTGCAGCGA | TGTCTCGCTC | CTGCTGCGTC | GCCGTGTCGG | TGCTTCTCGC | TGTCGCCGCG | 120 |
| ACAGCCAGCG | CCACCGCGCC | GGCATGGCTG | CACGAGGAGG | CCATGGCCAC | GGGCCCGCTG | 180 |
| GTCGCAGAGG | GTGCAAGGGT | GGCGCCCTCC | GCGTCCACCT | GGGCTGCCGA | CAAGGCGTCG | 240 |
| CCGGCGAGGC | CGAGCGGCGG | CATGGCCACG | CAGGCGACG | ACCAGAGCTC | GTCGGGCGGC | 300 |
| AGTGGCAGCA | GCGGTGAGCA | CGGCAAGGAG | GAGGGCGAGA | AGCAGGGCAA | GAGCTGCCTC | 360 |
| ACCAAGGAGG | AGTGCCACAA | GAAGAAGATG | ATCTGCGGCA | AGGGCTGCAC | GCTCTCGGCG | 420 |
| CACAGCAAGT | GCGCCGCCAA | GTGCACCAAG | TCCTGTGTCC | CACCTGCTA | GGAGCCGAGG | 480 |
| CCGGAGCTTG | CCGGCGGCGA | GACCTCGATC | GATCGAGTGC | TTCACTTCAC | TTCTTTGTTA | 540 |
| TAGTTCTTGT | GTGTTGCCGT | TGCGTTGCGT | TGCGTAGACG | AAGGGAATAA | GGAAGGGTAA | 600 |
| TTGGATTACC | TGTTCCAGAT | CTCTGTGTAA | GCGTGTTGTC | GTGACAAGTC | ATTTGATCCA | 660 |

| GAGCGAGCGA | TGGATAGATC | GCGCTCGCAG | TTTTAATTGC | AATGCTAGTT | CAATAAAAAA | 720 |
| AAAAAAAAAA | AAAAAAAAAA | AAAAAAAAAA | AAAAAAAAAA | AAAAAAAAAA | AAAAAAAAAA | 780 |
| CCATGGTACC | CGGATC | | | | | 796 |

( 2 ) INFORMATION FOR SEQ ID NO:3:

( i ) SEQUENCE CHARACTERISTICS:
        ( A ) LENGTH: 2784 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Corn
        ( F ) TISSUE TYPE: anther ( v i i ) IMMEDIATE SOURCE:
        ( B ) CLONE: Genomic DNA designated as pVG55.3

( i x ) FEATURE:
        ( A ) NAME/KEY: CDS
        ( B ) LOCATION: 1180..1596

( i x ) FEATURE:
        ( A ) NAME/KEY: TATA_signal
        ( B ) LOCATION: 1072

( i x ) FEATURE:
        ( A ) NAME/KEY: promoter
        ( B ) LOCATION: 1..1179

( i x ) FEATURE:
        ( A ) NAME/KEY: misc_feature
        ( B ) LOCATION: 1120..1839
        ( D ) OTHER INFORMATION: /function= "region corresponding to
            cDNA of SEQ ID NO:2"

( x i ) SEQUENCE DESCRIPTION: SEQ ID NO:3:

| TGGTATGCAT | CAATAGAGCC | GGAAGATGGT | CTGGAGTAAG | GACCTGGCAG | TGTGATACGG | 60 |
| GAACTTGACA | TCTGAATAGA | TATTCTCCCT | TGTCCCTCTG | GTAAAAAAAA | CTGTTGTCAC | 120 |
| ATTTGCCTTC | GCTGTGACTT | GGATGTATCA | TGTATATCTT | TGACCATTGA | TATCTTGGTT | 180 |
| AATCAGACGG | TGCATTACAA | TCATGGCCTC | ATTCATATAG | GGTTTAGGGT | TACCACGATT | 240 |
| GGTTTGCATA | AGTAGTACCC | CTCCGTTTCA | AATTATGTCG | TATTTTGATT | TTTTAGATAC | 300 |
| ACTTTTTATA | TAATTTTTTA | TTTTAAATTA | GGTGTTTTAT | ATAATACGTA | TCTAAGTGTA | 360 |
| TAATAAAATA | TATGTATCTA | AAAGCTGTAA | TTTAGTATAA | ATTAGAATGG | TGTATATCTT | 420 |
| CAATGTATGA | CAAATAATTT | GAAATGGAGG | AGGGTATGAA | AAGCCAAAAC | CTCCTAGAAT | 480 |
| ATGGAATGGA | GGGAATACAT | ACAAATTCTT | TGCTTCAGTT | AAAAGAAACG | AGAAAGGAG | 540 |
| GGGAATGGGG | AATCGTACTT | CAGTTTTTAC | GAGTTTTCAT | CAAACATGTA | TGCACGTCTT | 600 |
| CCCTTGGTTG | ATGCATCTTT | TTGGCAAATC | TTCGTTTAAT | TGCGGCTTCT | TTTTTATACC | 660 |
| GTTCGAAGGT | TTTCGTCGTC | AATGCTGAAA | CTCCACTTTC | ACCACCTTCG | GTTGCATCTG | 720 |
| CTTGCTTTCA | ATTCACCTCT | AATTAGTCCA | AGTGTTTCAT | TGGACGAAGG | TCCAAGTCCT | 780 |
| TCAGATCATC | TCAATTTTCT | TTGATCTGAA | ACAACAATTT | AAAACTGATT | TTGTTACCTT | 840 |
| GACCTGTCGA | AGACCTTCGA | ACGAACGGTA | CTGTAAAAAT | ACTGTACCTC | AGATTTGTGA | 900 |
| TTTCAATTCG | ATTCGGGTCT | CCTGGCTGGA | TGAAACCAAT | GCGAGAGAAG | AAGAAAAAAT | 960 |
| GTTGCATTAC | GCTCACTCGA | TCGGTTACGA | GCACGTAGTT | GGCGCCTGTC | ACCCAACCAA | 1020 |
| ACCAGTAGTT | GAGGCACGCC | CTGTTTGCTC | ACGATCACGA | ACGTACAGCA | CTATAAAACA | 1080 |

```
CGCAGGGACT GGAAAGCGAG ATTTCACAGC TCAAAGCAGC CAAAACGCAG AAGCTGCACT      1140

GCATATACAG AAGATACATC GAGCTAACTA GCTGCAGCG ATG TCT CGC TCC TGC          1194
                                           Met Ser Arg Ser Cys
                                            1               5

TGC GTC GCC GTG TCG GTG CTT CTC GCT GTC GCC GCG ACA GCC AGC GCC        1242
Cys Val Ala Val Ser Val Leu Leu Ala Val Ala Ala Thr Ala Ser Ala
             10              15                  20

ACC GCG CCG GCA TGG CTG CAC GAG GAG CAG CAC CTC GAG GAG GCC ATG        1290
Thr Ala Pro Ala Trp Leu His Glu Glu Gln His Leu Glu Glu Ala Met
         25              30                  35

GCC ACG GGC CCG CTG GTC GCA GAG GGT GCG AGG GTG GCG CCC TCC GCG        1338
Ala Thr Gly Pro Leu Val Ala Glu Gly Ala Arg Val Ala Pro Ser Ala
     40              45                  50

TCC ACC TGG GCT GCC GAC AAG GCG TCG CCG GCG AGG CCG AGC GGC GGC        1386
Ser Thr Trp Ala Ala Asp Lys Ala Ser Pro Ala Arg Pro Ser Gly Gly
 55              60                  65

ATG GCC ACG CAG GGC GAC GAC CAG AGC TCG TCG GGC GGC AGT GGC AGC        1434
Met Ala Thr Gln Gly Asp Asp Gln Ser Ser Ser Gly Gly Ser Gly Ser
 70              75                  80                  85

AGC GGT GAG CAC GGC AAG GCG GAG GGC GAG AAG CAG GGC AAG AGC TGC        1482
Ser Gly Glu His Gly Lys Ala Glu Gly Glu Lys Gln Gly Lys Ser Cys
             90                  95                 100

CTC ACC AAG GAG GAG TGC CAC AAG AAG AAG ATG ATC TGT GGC AAG GGC        1530
Leu Thr Lys Glu Glu Cys His Lys Lys Lys Met Ile Cys Gly Lys Gly
             105                 110                 115

TGC ACG CTC TCG GCG CAC AGC AAG TGC GCC GCC AAG TGC ACC AAG TCC        1578
Cys Thr Leu Ser Ala His Ser Lys Cys Ala Ala Lys Cys Thr Lys Ser
         120                 125                 130

TGT GTC CCC ACC TGC TAGGAGCCGA GGCCGGAGCT TGCCGGCGGC GAGACCTCGA        1633
Cys Val Pro Thr Cys
         135

TCGATCGAGT GCTTCACTTC ACTTCTTTGT TATAGTTCTT GTGTGTTGCC GTTGCGTTGC      1693

GTTGCGTAGA CGAAGGGAAT AAGGAAGGGT AATTGGATTA CCTGTTCCAG ATCTCTGTGT      1753

AAGCGTGTTG TCGTGACAAG TCTTTTGATC CAGAGCGAGG GATGGATAGA TCGCGCTCGC      1813

AGTTTTAATT GCAATGCTAG TTCAATATGT GTGCATCATG TTGGCAACTA CATAGTCCAG      1873

ATTCAAACCG AGATCGCTGT TTAGCATGCC AGCACAATAA TAACGGTACA ATCATATTAT      1933

ATTTTATACA AATGCACAAT TTATCTCTAG AGATGTCAAT GGGAAATTCC TCATCGGGTT      1993

ATATCATCTC AGACTCATCC CCATCATATT TGATTCATCC TCATACTCAT CCTCATATCT      2053

ATCATGAGTG CAAAACTCAT TTCATACCCA TCTCTATTTT GGTTTAGGGT CTCCATCCCT      2113

AATTAAGGGA TAACTAGTAC TAACAACTAG CACAAACTAT CTAGATTTCA GATATCACCA      2173

CATTGACAAA CAATCATCCA TGAACTATGA TCCATTCATC CATCCATCAA AAAATAAATC      2233

GGTATTTCGA GAACGATAGA AGAAATGAAG TCGGCTCACC TTTCTTGGTC ACCATTTGAG      2293

TTTGTTGGTG CCTGAGAATC CATGGTCGTC ATCGTCGTCC TAGGGATCGG CGGTGCTCCT      2353

CGTTGTTGGT AAAGTCGCCA GTGTGTAGTG CTAGCGCAAC TGTCCAGGCG TGCAACGGTT      2413

GGCCGGCTGG AAAGGGCATA GCGTATGGCT GGTTATTTTT AGGGTTTTGT TTTTTACTA      2473

ATCTGCTAGT TGCCTTGCCA TGTTGTCTTA TTGGGCTAGG ATCTAGGGCT TGTTACGCTG      2533

CTGTGTTGGG CTTGGTGTCC GGTTCAGCCT CAACTCATTC ATACAAATCA GATTCATACA      2593

AAACAGGTAT ACACGTATGA AATATCCATG GATAATCAGG TTCGAATTAT TGTCCCCTAA      2653

ACCCATACAC GTTACCCAA TGGATGGATA TTTTGTCTCA TATCCATACA CATGAGACGA      2713

TTTTTGTCCC ATACCTGTGC TCTAATAGGA GAATTTCTCT CGGGATAGCG AGTATCGGAT      2773
```

```
CCTCTAGAGT C                                                                                          2 7 8 4
```

( 2 ) INFORMATION FOR SEQ ID NO:4:

( i ) SEQUENCE CHARACTERISTICS:
        ( A ) LENGTH: 111 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Nicotiana tabacum cv. Samsun ( v i i ) IMMEDIATE SOURCE:
        ( B ) CLONE: TA36 intron with KpnI linkers at 5'and 3'
            ends ( i x ) FEATURE:
        ( A ) NAME/KEY: misc_feature
        ( B ) LOCATION: 1..7
        ( D ) OTHER INFORMATION: /function= "spacer sequence"

( i x ) FEATURE:
        ( A ) NAME/KEY: misc_feature
        ( B ) LOCATION: 8..13
        ( D ) OTHER INFORMATION: /product= "KpnI site"

( i x ) FEATURE:
        ( A ) NAME/KEY: intron
        ( B ) LOCATION: 16..100

( i x ) FEATURE:
        ( A ) NAME/KEY: misc_feature
        ( B ) LOCATION: 101..106
        ( D ) OTHER INFORMATION: /product= "KpnI site"

( i x ) FEATURE:
        ( A ) NAME/KEY: misc_feature
        ( B ) LOCATION: 107..111
        ( D ) OTHER INFORMATION: /function= "spacer sequence"

( x i ) SEQUENCE DESCRIPTION: SEQ ID NO:4:

```
CTACGACGGT  ACCACGTAAT  TAGTTTATAC  CTTTAAACTT  TAATTTTCAA  CCGATTTTGT        6 0

GTCGTCTGCT  TAATCTAACT  TATTGTTTTT  ATTACATACA  GGTACCCTAT  G                 1 1 1
```

( 2 ) INFORMATION FOR SEQ ID NO:5:

( i ) SEQUENCE CHARACTERISTICS:
        ( A ) LENGTH: 6376 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: pVE149 (plasmid DNA replicable in E. coli)

( i x ) FEATURE:
        ( A ) NAME/KEY: misc_feature
        ( B ) LOCATION: 1..396
        ( D ) OTHER INFORMATION: /function= "pUC18 derived DNA"

( i x ) FEATURE:
        ( A ) NAME/KEY: 3'UTR
        ( B ) LOCATION: 397..802
        ( D ) OTHER INFORMATION: /standard_name= "derived from
            nopaline synthese gene of Agrobacterium T-DNA"

( i x ) FEATURE:
        ( A ) NAME/KEY: CDS
        ( B ) LOCATION: 803..1223
        ( D ) OTHER INFORMATION: /function= "barnase coding sequence
            with TA36 intron"

( i x ) FEATURE:
    ( A ) NAME/KEY: intron
    ( B ) LOCATION: 1119..1203
    ( D ) OTHER INFORMATION: /standard_name= "TA36 intron"

( i x ) FEATURE:
    ( A ) NAME/KEY: misc_feature
    ( B ) LOCATION: 1224..2408
    ( D ) OTHER INFORMATION: /function= "CA55 promoter from corn"

( i x ) FEATURE:
    ( A ) NAME/KEY: misc_feature
    ( B ) LOCATION: 2409..3272
    ( D ) OTHER INFORMATION: /function= "35S3 promoter"

( i x ) FEATURE:
    ( A ) NAME/KEY: CDS
    ( B ) LOCATION: 3273..3824

( i x ) FEATURE:
    ( A ) NAME/KEY: 3'UTR
    ( B ) LOCATION: 3825..4127
    ( D ) OTHER INFORMATION: /function= "derived from nopaline synthase gene of Agrobacterium T-DNA"

( i x ) FEATURE:
    ( A ) NAME/KEY: misc_feature
    ( B ) LOCATION: 4138..6376
    ( D ) OTHER INFORMATION: /function= "pUC18 derived DNA"

( x i ) SEQUENCE DESCRIPTION: SEQ ID NO:5:

```
TCGCGCGTTT CGGTGATGAC GGTGAAAACC TCTGACACAT GCAGCTCCCG GAGACGGTCA      60
CAGCTTGTCT GTAAGCGGAT GCCGGGAGCA GACAAGCCCG TCAGGGCGCG TCAGCGGGTG     120
TTGGCGGGTG TCGGGGCTGG CTTAACTATG CGGCATCAGA GCAGATTGTA CTGAGAGTGC     180
ACCATATGCG GTGTGAAATA CCGCACAGAT GCGTAAGGAG AAAATACCGC ATCAGGCGCC     240
ATTCGCCATT CAGGCTGCGC AACTGTTGGG AAGGGCGATC GGTGCGGGCC TCTTCGCTAT     300
TACGCCAGCT GGCGAAAGGG GGATGTGCTG CAAGGCGATT AAGTTGGGTA ACGCCAGGGT     360
TTTCCCAGTC ACGACGTTGT AAAACGACGG CCAGTGAATT CGAGCTCGGT ACCCGGGGAT     420
CTTCCCGATC TAGTAACATA GATGACACCG CGCGCGATAA TTTATCCTAG TTTGCGCGCT     480
ATATTTTGTT TTCTATCGCG TATTAAATGT ATAATTGCGG GACTCTAATC ATAAAAACCC     540
ATCTCATAAA TAACGTCATG CATTACATGT TAATTATTAC ATGCTTAACG TAATTCAACA     600
GAAATTATAT GATAATCATC GCAAGACCGG CAACAGGATT CAATCTTAAG AAACTTTATT     660
GCCAAATGTT TGAACGATCT GCTTCGGATC CTCTAGAGNN NNCCGGAAAG TGAAATTGAC     720
CGATCAGAGT TTGAAGAAAA ATTTATTACA CACTTTATGT AAAGCTGAAA AAAACGGCCT     780
CCGCAGGAAG CCGTTTTTTT CGTTATCTGA TTTTTGTAAA GGTCTGATAA TGGTCCGTTG     840
TTTTGTAAAT CAGCCAGTCG CTTGAGTAAA GAATCCGGTC TGAATTTCTG AAGCCTGATG     900
TATAGTTAAT ATCCGCTTCA CGCCATGTTC GTCCGCTTTT GCCCGGGAGT TTGCCTTCCC     960
TGTTTGAGAA GATGTCTCCG CCGATGCTTT TCCCCGGAGC GACGTCTGCA AGGTTCCCTT    1020
TTGATGCCAC CCAGCCGAGG GCTTGTGCTT CTGATTTTGT AATGTAATTA TCAGGTAGCT    1080
TATGATATGT CTGAAGATAA TCCGCAACCC CGTCAAACTG TATGTAATAA AACAATAAG     1140
TTAGATTAAG CAGACGACAC AAAATCGGTT GAAAATTAAA GTTAAAGGT ATAAACTAAT     1200
TACGTGTTGA TAACCGGTAC CATGGCTGCA GCTAGTTAGC TCGATGTATC TTCTGTATAT    1260
GCAGTGCAGC TTCTGCGTTT TGGCTGCTTT GAGCTGTGAA ATCTCGCTTT CCAGTCCCTG    1320
CGTGTTTTAT AGTGCTGTAC GTTCGTGATC GTGAGCAAAC AGGGCGTGCC TCAACTACTG    1380
```

```
GTTTGGTTGG GTGACAGGCG CCAACTACGT GCTCGTAACC GATCGAGTGA GCGTAATGCA    1440
ACATTTTTC  TTCTTCTCTC GCATTGGTTT CATCCAGCCA GGAGACCCGA ATCGAATTGA    1500
AATCACAAAT CTGAGGTACA GTATTTTTAC AGTACCGTTC GTTCGAAGGT CTTCGACAGG    1560
TCAAGGTAAC AAAATCAGTT TTAAATTGTT GTTCAGATC  AAAGAAAATT GAGATGATCT    1620
GAAGGACTTG GACCTTCGTC CAATGAAACA CTTGGACTAA TTAGAGGTGA ATTGAAAGCA    1680
AGCAGATGCA ACCGAAGGTG GTGAAAGTGG AGTTTCAGCA TTGACGACGA AAACCTTCGA    1740
ACGGTATAAA AAAGAAGCCG CAATTAAACG AAGATTTGCC AAAAAGATGC ATCAACCAAG    1800
GGAAGACGTG CATACATGTT TGATGAAAAC TCGTAAAAAC TGAAGTACGA TTCCCCATTC    1860
CCCTCCTTTT CTCGTTTCTT TTAACTGAAG CAAAGAATTT GTATGTATTC CCTCCATTCC    1920
ATATTCTAGG AGGTTTTGGC TTTTCATACC CTCCTCCATT TCAAATTATT TGTCATACAT    1980
TGAAGATATA CACCATTCTA ATTTATACTA AATTACAGCT TTTAGATACA TATATTTTAT    2040
TATACACTTA GATACGTATT ATATAAAACA CCTAATTTAA AATAAAAAT  TATATAAAAA    2100
GTGTATCTAA AAAATCAAAA TACGACATAA TTTGAAACGG AGGGGTACTA CTTATGCAAA    2160
CCAATCGTGG TAACCCTAAA CCCTATATGA ATGAGGCCAT GATTGTAATG CACCGTCTGA    2220
TTAACCAAGA TATCAATGGT CAAAGATATA CATGATACAT CCAAGTCACA GCGAAGGCAA    2280
ATGTGACAAC AGTTTTTTTT ACCAGAGGGA CAAGGGAGAA TATCTATTCA GATGTCAAGT    2340
TCCCGTATCA CACTGCCAGG TCCTTACTCC AGACCATCTT CCGGCTCTAT TGATGCATAC    2400
CAGGAATTGA TCTAGAGTCG ACCTGCAGGC ATGCAAGCTC CTACGCAGCA GGTCTCATCA    2460
AGACGATCTA CCCGAGTAAC AATCTCCAGG AGATCAAATA CCTTCCCAAG AAGGTTAAAG    2520
ATGCAGTCAA AAGATTCAGG ACTAATTGCA TCAAGAACAC AGAGAAAGAC ATATTTCTCA    2580
AGATCAGAAG TACTATTCCA GTATGGACGA TTCAAGGCTT GCTTCATAAA CCAAGGCAAG    2640
TAATAGAGAT TGGAGTCTCT AAAAAGGTAG TTCCTACTGA ATCTAAGGCC ATGCATGGAG    2700
TCTAAGATTC AAATCGAGGA TCTAACAGAA CTCGCCGTGA AGACTGGCGA ACAGTTCATA    2760
CAGAGTCTTT TACGACTCAA TGACAAGAAG AAAATCTTCG TCAACATGGT GGAGCACGAC    2820
ACTCTGGTCT ACTCCAAAAA TGTCAAAGAT ACAGTCTCAG AAGACCAAAG GCTATTGAG     2880
ACTTTTCAAC AAAGGATAAT TTCGGGAAAC CTCCTCGGAT TCCATTGCCC AGCTATCTGT    2940
CACTTCATCG AAAGGACAGT AGAAAAGGAA GGTGGCTCCT ACAAATGCCA TCATTGCGAT    3000
AAAGGAAAGG CTATCATTCA AGATGCCTCT GCCGACAGTG GTCCCAAAGA TGGACCCCCA    3060
CCCACGAGGA GCATCGTGGA AAAAGAAGAC GTTCCAACCA CGTCTTCAAA GCAAGTGGAT    3120
TGATGTGACA TCTCCACTGA CGTAAGGGAT GACGCACAAT CCCACTATCC TTCGCAAGAC    3180
CCTTCCTCTA TATAAGGAAG TTCATTTCAT TTGGAGAGGA CACGCTGAAA TCACCAGTCT    3240
CTCTCTATAA ATCTATCTCT CTCTCTATAA CCATGGACCC AGAACGACGC CCGGCCGACA    3300
TCCGCCGTGC CACCGAGGCG GACATGCCGG CGGTCTGCAC CATCGTCAAC CACTACATCG    3360
AGACAAGCAC GGTCAACTTC CGTACCGAGC CGCAGGAACC GCAGGAGTGG ACGGACGACC    3420
TCGTCCGTCT GCGGGAGCGC TATCCCTGGC TCGTCGCCGA GGTGGACGGC GAGGTCGCCG    3480
GCATCGCCTA CGCGGGCCCC TGGAAGGCAC GCAACGCCTA CGACTGGACG GCCGAGTCGA    3540
CCGTGTACGT CTCCCCCCGC CACCAGCGGA CGGGACTGGG CTCCACGCTC TACACCCACC    3600
TGCTGAAGTC CCTGGAGGCA CAGGGCTTCA AGAGCGTGGT CGCTGTCATC GGGCTGCCCA    3660
ACGACCCGAG CGTGCGCATG CACGAGGCGC TCGGATATGC CCCCGCGGC  ATGCTGCGGG    3720
CGGCCGGCTT CAAGCACGGG AACTGGCATG ACGTGGGTTT CTGGCAGCTG GACTTCAGCC    3780
```

```
TGCCGGTACC GCCCCGTCCG GTCCTGCCCG TCACCGAGAT CTGATCTCAC GCGTCTAGGA  3840
TCCGAAGCAG ATCGTTCAAA CATTTGGCAA TAAAGTTTCT TAAGATTGAA TCCTGTTGCC  3900
GGTCTTGCGA TGATTATCAT ATAATTTCTG TTGAATTACG TTAAGCATGT AATAATTAAC  3960
ATGTAATGCA TGACGTTATT TATGAGATGG GTTTTATGA TTAGAGTCCC GCAATTATAC  4020
ATTTAATACG CGATAGAAAA CAAATATAG CGCGCAAACT AGGATAAATT ATCGCGCGCG  4080
GTGTCATCTA TGTTACTAGA TCGGGAAGAT CCTCTAGAGT CGACCTGCAG GCATGCAAGC  4140
TTGGCGTAAT CATGGTCATA GCTGTTTCCT GTGTGAAATT GTTATCCGCT CACAATTCCA  4200
CACAACATAC GAGCCGGAAG CATAAAGTGT AAAGCCTGGG GTGCCTAATG AGTGAGCTAA  4260
CTCACATTAA TTGCGTTGCG CTCACTGCCC GCTTTCCAGT CGGGAAACCT GTCGTGCCAG  4320
CTGCATTAAT GAATCGGCCA ACGCGCGGGG AGAGGCGGTT TGCGTATTGG GCGCTCTTCC  4380
GCTTCCTCGC TCACTGACTC GCTGCGCTCG GTCGTTCGGC TGCGGCGAGC GGTATCAGCT  4440
CACTCAAAGG CGGTAATACG GTTATCCACA GAATCAGGGG ATAACGCAGG AAAGAACATG  4500
TGAGCAAAAG GCCAGCAAAA GGCCAGGAAC CGTAAAAAGG CCGCGTTGCT GGCGTTTTTC  4560
CATAGGCTCC GCCCCCCTGA CGAGCATCAC AAAAATCGAC GCTCAAGTCA GAGGTGGCGA  4620
AACCCGACAG GACTATAAAG ATACCAGGCG TTTCCCCCTG GAAGCTCCCT CGTGCGCTCT  4680
CCTGTTCCGA CCCTGCCGCT TACCGGATAC CTGTCCGCCT TTCTCCCTTC GGGAAGCGTG  4740
GCGCTTTCTC AATGCTCACG CTGTAGGTAT CTCAGTTCGG TGTAGGTCGT TCGCTCCAAG  4800
CTGGGCTGTG TGCACGAACC CCCCGTTCAG CCCGACCGCT GCGCCTTATC CGGTAACTAT  4860
CGTCTTGAGT CCAACCCGGT AAGACACGAC TTATCGCCAC TGGCAGCAGC CACTGGTAAC  4920
AGGATTAGCA GAGCGAGGTA TGTAGGCGGT GCTACAGAGT TCTTGAAGTG GTGGCCTAAC  4980
TACGGCTACA CTAGAAGGAC AGTATTTGGT ATCTGCGCTC TGCTGAAGCC AGTTACCTTC  5040
GGAAAAAGAG TTGGTAGCTC TTGATCCGGC AAACAAACCA CCGCTGGTAG CGGTGGTTTT  5100
TTTGTTTGCA AGCAGCAGAT TACGCGCAGA AAAAAGGAT CTCAAGAAGA TCCTTTGATC  5160
TTTTCTACGG GGTCTGACGC TCAGTGGAAC GAAAACTCAC GTTAAGGGAT TTTGGTCATG  5220
AGATTATCAA AAAGGATCTT CACCTAGATC CTTTTAAATT AAAAATGAAG TTTTAAATCA  5280
ATCTAAAGTA TATATGAGTA AACTTGGTCT GACAGTTACC AATGCTTAAT CAGTGAGGCA  5340
CCTATCTCAG CGATCTGTCT ATTTCGTTCA TCCATAGTTG CCTGACTCCC CGTCGTGTAG  5400
ATAACTACGA TACGGGAGGG CTTACCATCT GGCCCCAGTG CTGCAATGAT ACCGCGAGAC  5460
CCACGCTCAC CGGCTCCAGA TTTATCAGCA ATAAACCAGC CAGCCGGAAG GGCCGAGCGC  5520
AGAAGTGGTC CTGCAACTTT ATCCGCCTCC ATCCAGTCTA TTAATTGTTG CCGGGAAGCT  5580
AGAGTAAGTA GTTCGCCAGT TAATAGTTTG CGCAACGTTG TTGCCATTGC TACAGGCATC  5640
GTGGTGTCAC GCTCGTCGTT TGGTATGGCT TCATTCAGCT CCGGTTCCCA ACGATCAAGG  5700
CGAGTTACAT GATCCCCCAT GTTGTGCAAA AAAGCGGTTA GCTCCTTCGG TCCTCCGATC  5760
GTTGTCAGAA GTAAGTTGGC CGCAGTGTTA TCACTCATGG TTATGGCAGC ACTGCATAAT  5820
TCTCTTACTG TCATGCCATC CGTAAGATGC TTTTCTGTGA CTGGTGAGTA CTCAACCAAG  5880
TCATTCTGAG AATAGTGTAT GCGGCGACCG AGTTGCTCTT GCCCGGCGTC AATACGGGAT  5940
AATACCGCGC CACATAGCAG AACTTTAAAA GTGCTCATCA TTGGAAAACG TTCTTCGGGG  6000
CGAAAACTCT CAAGGATCTT ACCGCTGTTG AGATCCAGTT CGATGTAACC CACTCGTGCA  6060
CCCAACTGAT CTTCAGCATC TTTTACTTTC ACCAGCGTTT CTGGGTGAGC AAAAACAGGA  6120
AGGCAAAATG CCGCAAAAAA GGGAATAAGG GCGACACGGA AATGTTGAAT ACTCATACTC  6180
```

```
TTCCTTTTTC  AATATTATTG  AAGCATTTAT  CAGGGTTATT  GTCTCATGAG  CGGATACATA    6240

TTTGAATGTA  TTTAGAAAAA  TAAACAAATA  GGGGTTCCGC  GCACATTTCC  CCGAAAAGTG    6300

CCACCTGACG  TCTAAGAAAC  CATTATTATC  ATGACATTAA  CCTATAAAAA  TAGGCGTATC    6360

ACGAGGCCCT  TTCGTC                                                        6376
```

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: nucleotides 64-85 of pCA444

( x i ) SEQUENCE DESCRIPTION: SEQ ID NO:6:

```
CCGAGGACCA  GCAGGACGAG  GC                                                  22
```

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: nucleotides 358 to 377 of pCA444

( x i ) SEQUENCE DESCRIPTION: SEQ ID NO:7:

```
GGATGGCAGG  AGGGGAGAGG                                                      20
```

( 2 ) INFORMATION FOR SEQ ID NO:8:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: nucleotides 22 to 43 of pCA444

( x i ) SEQUENCE DESCRIPTION: SEQ ID NO:8:

```
GGGGCGGTGG  CTGCTTCTAG  CG                                                  22
```

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: nucleotides 74 to 93 of pCA444

( x i ) SEQUENCE DESCRIPTION: SEQ ID NO:9:

```
GCTGGTCCTC  GGCGGCGGCA                                                      20
```

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: nucleotides 34 to 54 of pCA455

( x i ) SEQUENCE DESCRIPTION: SEQ ID NO:10:

GCTCGATGTA TGCAGTGCAG C        21

( 2 ) INFORMATION FOR SEQ ID NO:11:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: nucleotides 87 to 109 of pCA455

( x i ) SEQUENCE DESCRIPTION: SEQ ID NO:11:

CGTCGCCGTG TCGGTGCTTC TCG        23

( 2 ) INFORMATION FOR SEQ ID NO:12:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: nucleotides 557 to 580 of pCA455

( x i ) SEQUENCE DESCRIPTION: SEQ ID NO:12:

CCGTTGCGTT GCGTTGCGTA GACG        24

( 2 ) INFORMATION FOR SEQ ID NO:13:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

CAGGAGCGAG CCATGGCTGC AG        22

( 2 ) INFORMATION FOR SEQ ID NO:14:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

GATTCGAATT CTGGTATGCA TCAATAGAGC CG 32

( 2 ) INFORMATION FOR SEQ ID NO:15:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

GATAACCGGT ACCATGGTTG TCACAGGGG 29

( 2 ) INFORMATION FOR SEQ ID NO:16:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

CCCCGTCAAA TGCATTGATA ACCGG 25

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

CGACGGTACC ACGTAATTAG 20

( 2 ) INFORMATION FOR SEQ ID NO:18:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

CATAGGGTAC CTGTATGTAA TAAAAAC 27

( 2 ) INFORMATION FOR SEQ ID NO:19:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

GCTTTTTTAA ATTTATTTTC TCC 23

(2) INFORMATION FOR SEQ ID NO:20:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(vii) IMMEDIATE SOURCE:
(B) CLONE: nucleotides 269 to 288 of pCA444

(xi) SEQUENCE DESCRIPTION: SEQ ID NO:20:

GCAGGCTGTT GATGATGCCC   20

(2) INFORMATION FOR SEQ ID NO:21:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: DNA (genomic)

(vii) IMMEDIATE SOURCE:
(B) CLONE: nucleotides 392 to 414 of pCA444

(xi) SEQUENCE DESCRIPTION: SEQ ID NO:21:

CCATTTCACA GTGAGAGCAG TCG   23